(12) United States Patent
Hammes et al.

(10) Patent No.: US 11,302,436 B2
(45) Date of Patent: Apr. 12, 2022

(54) METHOD, COMPUTER AND MEDICAL IMAGING APPARATUS FOR THE PROVISION OF CONFIDENCE INFORMATION

(71) Applicant: Siemens Healthcare GmbH, Erlangen (DE)

(72) Inventors: Martin Hammes, Erlangen (DE); Bjoern Heismann, Erlangen (DE); Rene Kartmann, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 450 days.

(21) Appl. No.: 15/726,621

(22) Filed: Oct. 6, 2017

(65) Prior Publication Data
US 2018/0101644 A1    Apr. 12, 2018

(30) Foreign Application Priority Data
Oct. 7, 2016    (DE) .......................... 102016219488.7

(51) Int. Cl.
*G16H 40/00* (2018.01)
*G16H 30/40* (2018.01)
(Continued)

(52) U.S. Cl.
CPC ............. *G16H 30/40* (2018.01); *A61B 5/055* (2013.01); *A61B 5/7267* (2013.01);
(Continued)

(58) Field of Classification Search
CPC ... G16H 50/20; G16H 40/20; G06Q 50/22–24
See application file for complete search history.

(56) References Cited

U.S. PATENT DOCUMENTS 6,662,051 B1 * 12/2003 Eraker ............... A61N 1/36021
607/59
2005/0049497 A1    3/2005 Krishnan et al.
(Continued)

FOREIGN PATENT DOCUMENTS

| CN | 1762304 A | 4/2006 |
| CN | 1839391 A | 9/2006 |

(Continued)

OTHER PUBLICATIONS

Office Acion dated May 19, 202 for Chinese Patent Application No. 201710915757.7 (with English translation).

*Primary Examiner* — John A Pauls
(74) *Attorney, Agent, or Firm* — Banner & Witcoff, Ltd.

(57) ABSTRACT

In a method, computer and medical imaging apparatus for the provision of confidence information, an automatic diagnosis system is provided to the computer. Medical image data acquired from a patient are received by or accessed by the computer. A measure of confidence is determined by the computer, which describes the reliability of a correct diagnosis of the medical image data by the diagnosis system. The confidence information concerning the reliability of the correct diagnosis of the medical image data by the diagnosis system is provided as an output from the computer, wherein the confidence information is based on the determined measure of confidence.

18 Claims, 2 Drawing Sheets

(51) Int. Cl.

| | | |
|---|---|---|
| *G06K 9/62* | (2022.01) | |
| *G16H 50/20* | (2018.01) | |
| *A61B 5/055* | (2006.01) | |
| *A61B 5/00* | (2006.01) | |
| *G06T 7/00* | (2017.01) | |
| *A61B 6/00* | (2006.01) | |
| *A61B 8/00* | (2006.01) | |
| *A61B 6/03* | (2006.01) | |
| *A61B 8/08* | (2006.01) | |

(52) U.S. Cl.
CPC .......... *G06K 9/6201* (2013.01); *G06T 7/0012* (2013.01); *G16H 50/20* (2018.01); *A61B 6/032* (2013.01); *A61B 6/037* (2013.01); *A61B 6/468* (2013.01); *A61B 6/5217* (2013.01); *A61B 8/00* (2013.01); *A61B 8/468* (2013.01); *A61B 8/5223* (2013.01); *A61B 2576/02* (2013.01); *G06K 2209/05* (2013.01); *G06T 2207/10088* (2013.01); *G06T 2207/20081* (2013.01); *G06T 2207/30168* (2013.01)

(56) References Cited

U.S. PATENT DOCUMENTS

| | | | | |
|---|---|---|---|---|
| 2005/0251013 | A1* | 11/2005 | Krishnan | G06T 7/0012 600/407 |
| 2006/0100507 | A1 | 5/2006 | Mertelmeier | |
| 2006/0210131 | A1* | 9/2006 | Wheeler, Jr. | G06T 11/008 382/128 |
| 2007/0165924 | A1 | 7/2007 | Nicponski | |
| 2008/0219530 | A1 | 9/2008 | Levanon et al. | |
| 2009/0080741 | A1* | 3/2009 | Shinagawa | G06K 9/4609 382/131 |
| 2009/0092300 | A1* | 4/2009 | Jerebko | G06K 9/6278 382/128 |
| 2009/0136107 | A1 | 5/2009 | Arnold et al. | |
| 2009/0136113 | A1* | 5/2009 | Chan | A61B 6/502 382/132 |
| 2010/0121178 | A1 | 5/2010 | Krishnan et al. | |
| 2010/0246912 | A1* | 9/2010 | Periaswamy | G06K 9/00 382/131 |
| 2010/0256459 | A1 | 10/2010 | Miyasa et al. | |
| 2011/0087089 | A1* | 4/2011 | Meinel | A61B 6/502 600/411 |
| 2012/0023042 | A1* | 1/2012 | Das | G06N 7/005 706/12 |
| 2012/0256920 | A1* | 10/2012 | Marshall | A61B 8/0825 345/420 |
| 2014/0046889 | A1* | 2/2014 | Biem | G06F 16/24568 706/46 |
| 2014/0288440 | A1* | 9/2014 | Asher | A61B 5/082 600/484 |
| 2015/0117737 | A1 | 4/2015 | Kim et al. | |
| 2016/0069973 | A1* | 3/2016 | Fenchel | G01R 33/481 324/309 |
| 2019/0223845 | A1* | 7/2019 | Podilchuk | A61B 10/0041 |

FOREIGN PATENT DOCUMENTS

| | | |
|---|---|---|
| CN | 101366059 A | 2/2009 |
| CN | 101808574 A | 8/2010 |
| CN | 104573309 A | 4/2015 |

* cited by examiner

METHOD, COMPUTER AND MEDICAL IMAGING APPARATUS FOR THE PROVISION OF CONFIDENCE INFORMATION

BACKGROUND OF THE INVENTION

Field of the Invention

The present invention concerns a method for the provision of confidence information, and a computer, and a medical imaging apparatus for implementing such a method.

Description of the Prior Art

Medical image data are normally recorded with a medical imaging apparatus and can represent anatomical structures and/or functional processes of the body of a patient.

Methods from applied artificial intelligence research, such as for example deep learning, are being applied increasingly to medical image data and/or combinations thereof with other patient data. It is foreseeable that it will be possible for radiological diagnoses of medical image data to be gradually supplemented by, or even taken over by computers. In this way it is possible to lessen the workload on radiologists, for example in routine situations. Computer-aided evaluations can also enable new applications that are too complicated for humans.

A major hurdle for acceptance of diagnosis of medical image data by machine is guaranteeing a satisfactory level of quality or reliability of the machine diagnosis. Normally, radiological diagnoses are produced by humans and responsibility therefor is taken by humans. As soon as a computer produces a diagnosis semi-autonomously or autonomously, it appears appropriate to be obliged to validate the diagnosis in clinical reality.

SUMMARY OF THE INVENTION

The object of the invention is to determine and provide confidence information for an automatic diagnosis system.

The method according to the invention for the provision of confidence information has the following method steps:
provision of an automatic diagnosis system,
acquisition of medical image data for a patient,
determination of a measure of confidence which describes a reliability of a correct diagnosis of the medical image data by the diagnosis system, and
provision of confidence information concerning the reliability of the correct diagnosis of the medical image data by the diagnosis system, wherein the confidence information is based on the determined measure of confidence.

As used herein, diagnosis refers to a diagnostic assessment, for example in the form of a standardized annotation format. Diagnosis can also be considered as a report about a presence of certain clinical features in the patient, for example a presence of a tumor or some other illness which can be detected in the medical image data. The diagnosis can alternatively or additionally also include details of general irregularities or abnormalities in the medical image data.

In this context the provision of the diagnosis system can involve calling or loading the diagnosis system from a database and/or an electronically readable data medium. In particular, such a diagnosis system is provided that is suitable for the diagnosis of the medical image data. The diagnosis system can be designed in order to analyze the medical image data in relation to a specific diagnostic investigation. Such a specific diagnostic investigation can be, for example, the presence of a specific tumor, for example a suspicious lesion in the breast, a rectal carcinoma, a tumor mass in the lung, a prostate carcinoma, etc. The specific diagnostic investigation can alternatively be the automatic identification of the existence of a vascular disease, such as a coronary heart disease and/or a congenital heart defect. The specific diagnostic investigation can also involve neurological investigations, such as identification of the existence of Alzheimer's disease or preliminary stages thereof, or the detection of multiple sclerosis lesions. Further possible specific diagnostic investigations are known to those skilled in the art. The diagnosis system can alternatively or additionally be designed for the general detection of irregularities or abnormalities in medical image data.

The diagnosis system is designed as an algorithm that uses, as its input data, the medical image data and possibly further patient specific data, and produces output data in the form of a diagnosis of the medical image data. Alternatively or additionally, the diagnosis system can be designed in order to support a radiologist who produces the final diagnosis. In this situation, the diagnosis system can feature machine-based artificial intelligence. For example, the diagnosis system can employ an artificial neural network. In this situation the diagnosis system can employ known methods covered by the concept of "deep learning". The diagnosis system can alternatively or additionally employ known automatic classification algorithms, such as Bayes classifiers or support vector machines (SVM). The diagnosis system can furthermore employ algorithms for structure analysis and/or preprocessing and/or segmentation of the medical image data. Different further possible forms of an automatic diagnosis system are known to those skilled in the art so they need not be discussed in detail herein.

The acquisition of the medical image data can involve recording the medical image data by operation of a medical imaging apparatus, or loading the medical image data from a database.

The measure of confidence can be determined by a determination processor. The measure of confidence can be determined by execution of a determination algorithm that has as its input parameter at least one characteristic value for the diagnosis system, possibly supplemented by metainformation and/or an image content from medical image data, and as its output parameter the measure of confidence. The at least one characteristic value for the diagnosis system can, as described in further detail below, characterize a mean accuracy of the diagnosis system, for example a sensitivity and/or specificity, of the diagnosis system.

The measure of confidence that is determined characterizes the reliability of a correct diagnosis by the diagnosis system specifically with regard to the medical image data. This means that the determined measure of confidence applies exclusively to the specific case of the diagnosis of the medical image data acquired from the patient. It is alternatively also conceivable for the measure of confidence to describe a general reliability of the correct diagnosis by the diagnosis system. In this context the measure of confidence can be a number or a percentage. The measure of confidence can therefore directly quantify the reliability of the correct diagnosis. The measure of confidence can alternatively also involve a classification of the reliability of the correct diagnosis into different reliability classes, such as "high reliability", "low reliability". The confidence information can alternatively or additionally include decision information, which can serve as the basis for a subsequent decision, and/or instructions for controlling further processing. The measure of confidence can be formed directly from the confidence information that is ultimately provided. The confidence information can directly be the determined measure of confidence, or an informational item derived from the determined measure of confidence.

The provision of the confidence information can be an output of the confidence information on an output unit, for example a display monitor. Alternatively or additionally, the confidence information can be made available to another-processor for further processing. The provision of the confidence information can be forwarding the confidence information or the measure of confidence to a decision computer. The provision of the confidence information can alternatively or additionally involve saving the confidence information, in particular for documentation purposes. In this situation the provision of the confidence information can directly be provision of the measure of confidence.

The provision of the confidence information offers an opportunity to evaluate whether the diagnosis system is suitable for automatic diagnosis of the medical image data. The confidence information provided can thus facilitate or enable a decision as to whether the diagnosis is to be performed by the diagnosis system. The confidence information that is provided can also play an important role with respect to regulatory prerequisites concerning use of the diagnosis system.

In an embodiment, a decision is made on the basis of the measure of confidence as to whether the medical image data are diagnosed automatically by the diagnosis system, or whether the medical image data is presented to a radiologist for diagnosis.

The decision can be made automatically by a decision unit, to which the measure of confidence is presented, or manually, for example by a radiologist. If the measure of confidence or the confidence information provided indicates that a high level of reliability of the correct diagnosis of the medical image data by the diagnosis system exists, then the decision can be made that the medical image data are diagnosed automatically by the diagnosis system. Otherwise the decision is expedient that the medical image data are diagnosed manually by the radiologist or that the diagnosis system merely supports the radiologist in the diagnosis of the medical image data. If the decision is made that the medical image data are to be presented to a radiologist for the diagnosis, the decision can be expanded. In this situation an expansion of the decision is conceivable such that a decision is additionally made as to whether the diagnosis is to be performed exclusively manually by the radiologist or that an automatic diagnosis is initially to be performed by the diagnosis system, in which case the automatic diagnosis then only needs to be checked by the radiologist. It is conceivable for a decision to be made on the basis of the measure of confidence as to whether a diagnosis of the medical image data by the diagnosis system needs to be checked by a radiologist.

The medical image data can be further processed automatically on the basis of the decision that is made. The decision that is made can thus be stored as metadata for the medical image data. The further processing of the medical image data on the basis of the decision can involve, for example, the medical image data being given to the diagnosis system for the diagnosis, or the medical image data being placed on a work list for the radiologist. The measure of confidence can in this manner offer a particularly advantageous basis for the decision as to whether the diagnosis can be performed by a radiologist alone, by a combination of the radiologist and the diagnosis system, or by the diagnosis system alone.

In an embodiment the decision is made on the basis of the confidence information provided.

To this end, the provision of the confidence information involves an output of the confidence information, for example on a display monitor. The decision can then be made, for example by a radiologist, on the basis of the confidence information that is shown. The confidence information can offer the radiologist valuable information as to the extent to which he or she can rely on the diagnosis by the diagnosis system. The confidence information can also give the radiologist an indication as to how much time he or she may need to spend in order to check the diagnosis made by the diagnosis system.

In another embodiment, the decision is made automatically on the basis of the measure of confidence, and the provision of the confidence information involves provision of the decision.

In this case the decision is made automatically by the decision processor that uses the measure of confidence as an input parameter for the decision. To this end, the measure of confidence determined by the determination processor can be passed to the decision processor. The decision that the medical image data are to be diagnosed automatically by the diagnosis system is made when a high measure of confidence that confirms a level of reliability of the diagnosis by the diagnosis system has been determined. The provision of the decision is designed in order to define the further processing of the medical image data, in particular with respect to the diagnosis of the medical image data.

In another embodiment, the decision is made automatically on the basis of a threshold value comparison of the measure of confidence with at least one threshold value for the measure of confidence.

In the simplest case a threshold value can be defined for the measure of confidence. If the measure of confidence lies above the threshold value, then the decision can be made that the medical image data be diagnosed automatically by the diagnosis system. If the measure of confidence lies below the threshold value, then the decision can be made that the medical image data be presented to a radiologist for the diagnosis. The reverse situation is naturally also conceivable, in which a lower measure of confidence expresses a high level of reliability of the automatic diagnosis by the diagnosis system. It is also possible to define a number of threshold values. In this manner it is possible to make more finely differentiated decisions, for example that although the diagnosis can be performed by the diagnosis system, it must subsequently still be checked by a radiologist.

The threshold value comparison offers a particularly simple way of making the decision. At the same time the threshold value comparison enables an adjustment of the at least one threshold value customized to the individual wishes of the user. Further options are naturally also conceivable as to how the decision can be made automatically on the basis of the measure of confidence.

In the following, different parameters (first parameter, second parameter, third parameter, fourth parameter, fifth parameter, sixth parameter) are described which are taken into consideration during the determination of the measure of confidence. During the determination of the measure of confidence at least one of the parameters described in the following can thus be taken into consideration. It is also conceivable to take into consideration any desired combination of the parameters described in the following during the determination of the measure of confidence. The fact that the measure of confidence is determined using or taking into consideration one of the following parameters means that the determination algorithm for determining the measure of confidence has that parameter as an input parameter. The formulation that the measure of confidence is determined by using a parameter that is determined on the basis of an input variable can also involve the measure of confidence being determined directly by using the input variable.

In an embodiment, the measure of confidence is determined by using a first parameter that characterizes a mean accuracy of the diagnosis system.

The first parameter is determined during a clinical validation and/or training of the diagnosis system and/or during actual clinical operation. One option for determining the first parameter is for the first parameter to be independent of the configuration of the medical image data to be specifically diagnosed. In this manner the first parameter can characterize the general reliability of the diagnosis system with respect to the diagnosis of medical image data.

The first parameter can be based on a sensitivity and/or specificity of the diagnosis system, or can be the sensitivity and/or specificity of the diagnosis system. In this context the first parameter is targeted at a sensitivity and/or specificity of the diagnosis system in relation to the specific diagnosis that the diagnosis system is to perform in the medical image data. Alternatively or additionally, the first parameter can be based on an absolute detection rate of the diagnosis system, or be the absolute detection rate of the diagnosis system.

In an embodiment, the first parameter is determined by means of the following steps:

provision of medical training image data, for which a manual diagnosis by the radiologist exists, application of the diagnosis system to the medical training image data, wherein an automatic diagnosis of the medical training image data is produced, determination of the first parameter on the basis of a degree of correspondence of the manual diagnosis and the automatic diagnosis of the medical training image data.

The medical training image data can be made available in dedicated fashion in order to determine the first parameter. The medical training image data in question can also be image data that are acquired continuously during clinical operation, or that are diagnosed by the diagnosis system during clinical operation. As described in more detail in the following embodiment, the medical training image data in question can also be image data by which the diagnosis system is trained.

The medical training image data are characterized by respective manual diagnoses by a radiologist being able to be made in each case. In this context the manual diagnosis can be a written or oral diagnostic assessment. The medical training image data are stored together with the manual diagnosis in a training database. This involves a multiplicity of different medical training image data sets that have been acquired from different patients, with the respective associated saved manual diagnoses. In this manner the provision of the medical training image data can be loading the medical training image data together with the respective manual diagnosis from the database.

The manual diagnosis is saved in a standardized annotation format, as is defined, for example, by an association of radiologists. The standardized annotation format can be machine readable, so that it is possible to determine the degree of correspondence of the manual diagnosis and automatic diagnosis in a simple fashion.

As noted above, the diagnosis system is applied to the medical image data independently of the manual diagnosis, so the automatic diagnosis is performed by the diagnosis system independently of the manual diagnosis. The sequence of performing the automatic diagnosis and manual diagnosis is accordingly unimportant. Both diagnoses can be performed so as to at least partially overlap in time.

In order to determine the first parameter a comparison, in particular an automatic comparison, of the manual diagnosis and automatic diagnosis of the medical image data is performed. In the comparison, the degree of correspondence between the manual diagnosis and the automatic diagnosis are determined. For example, it is possible in the comparison to determine in how many cases the automatic diagnosis by the diagnosis system delivers the same result as the manual diagnosis by the radiologist.

The first parameter can be derived directly from the degree of correspondence, or can be the degree of correspondence. Generally speaking, a high degree of correspondence between the manual diagnosis and the automatic diagnosis suggests that the automatic diagnosis is performed correctly with a high level of reliability. In this manner the existence of a high degree of correspondence can have the result that the first parameter indicates a high mean accuracy to the diagnosis system. It is then in turn possible to determine a measure of confidence on the basis of the first parameter, which describes a high level of reliability of the correct diagnosis of the medical image data by the diagnosis system. In the reverse situation the reliability of the correct diagnosis by the diagnosis system is likely to be low if the manual diagnoses and automatic diagnoses of the medical training image data differ significantly.

The inventive procedure that provides for the use of medical training image data can thus produce a meaningful determination of the mean accuracy of the diagnosis system. In this case, the mean accuracy of the diagnosis system can be updated continuously during clinical operation of the diagnosis system as long as manual diagnoses by a radiologist exist.

In an embodiment, parameters of the diagnosis system are adjusted on the basis of the degree of correspondence of the manual diagnosis and the automatic diagnosis.

In this manner, not only is the first parameter determined by the described procedure, but also the diagnosis system itself is also adjusted. In this manner, training of the diagnosis system can take place using the medical training image data. The diagnosis system is able to learn on the basis of the medical training image data and the corresponding saved manual diagnosis. In this situation the parameters for the diagnosis system are adjusted such that a degree of correspondence between the manual diagnoses and automatic diagnoses is increased. The diagnosis system thus can be improved and at the same time validated with respect to the diagnostic accuracy.

In another embodiment, the measure of confidence is determined by using a second parameter, the second parameter being determined on the basis of the medical image data for the patient.

The medical image data are accordingly employed directly as an input parameter in the determination of the second parameter that is used for calculating the measure of confidence. In this case an image content from medical image data and/or metainformation, which is stored for the medical image data, for example in a DICOM format, can be employed in the determination of the second parameter. In this situation the metainformation can be, for example, demographic patient information, such as the age and/or gender of the patient. Further metainformation relating to the medical image data, such as stored acquisition parameters, are naturally conceivable. In this manner the determination of the measure of confidence on the basis of the medical image data can take place in coordination with the concrete diagnosis of the medical image data for the patient.

In an embodiment, a measure of quality is produced for the medical image data on the basis of the medical image data, with the second parameter being determined on the basis of the measure of quality.

The measure of quality can be derived directly from the image content from medical image data and/or from metainformation that is stored for the medical image data. The measure of quality can be, for example, a signal-to-noise ratio (SNR) or contrast-to-noise ratio (CNR) of the medical image data, or can be based on those parameters. The measure of quality can be determined on the basis of an incidence of artifacts in the medical image data. The measure of quality can characterize the suitability of the medical image data for automatic diagnosis by the diagnosis system. Medical image data having a poorer image quality or having artifacts can actually typically be diagnosed more reliably by a human being than by an automatic system. The measure of quality can be employed as the second parameter in the determination of the measure of confidence such that a higher image quality or lower incidence of artifacts results in a higher level of reliability of a correct diagnosis of the medical image data by the diagnosis system.

In another embodiment, the medical image data include a number of medical image data sets for the patient, and the diagnosis system produces a number of independent diagnoses separately for the multiple medical image data sets, and the measure of confidence is determined using a third parameter, with the third parameter being determined on the basis of a degree of correspondence of the multiple of independent diagnoses.

The multiple medical image data sets are recorded from the same patient. The multiple medical image data sets can be acquired using the same imaging modality or using different imaging modalities. If the multiple medical image data sets are recorded using the same imaging modality, then the multiple medical image data sets are recorded sequentially, in particular in one recording session. If the multiple medical image data sets are recorded using different imaging modalities, in the case of integrated imaging devices a simultaneous acquisition of the multiple medical image data sets is conceivable. The multiple medical image data sets can respectively exhibit differing image contrasts. If the multiple medical image data sets are acquired by magnetic resonance imaging, then the multiple medical image data sets can be acquired, for example, by differing magnetic resonance sequences.

The diagnosis of the multiple medical image data sets by the diagnosis system includes a first diagnosis of a first medical image data set of the multiple medical image data sets and a second diagnosis of a second medical image data set of the multiple medical image data sets. In this case the first diagnosis and the second diagnosis are performed independently of one another so that no information from the first diagnosis influences the second diagnosis, and vice versa. A degree of correspondence of the first diagnosis and the second diagnosis can subsequently be determined by comparing the diagnosis results from the first diagnosis and the second diagnosis, for example. If the first diagnosis and the second diagnosis indicate the same diagnosis result, then a high degree of correspondence of the multiple independent diagnoses can be determined. This procedure can be easily extended to more than two medical image data sets, in other words more than two diagnoses. The third parameter can in principle be determined more reliably if a high number of multiple medical image data sets are diagnosed independently of one another, and the respective diagnoses are compared.

This procedure for determining the measure of confidence is based on the consideration that a high degree of correspondence of the multiple independent diagnoses can in principle indicate a higher level of reliability of the correct diagnosis by the diagnosis system. If, for example, all the independent diagnoses involve the same diagnosis result, then a higher level of reliability can be associated with the diagnosis system than if only half of the independent diagnoses involves the same diagnosis result, or if some of the independent diagnoses differ from one another.

In another embodiment, the measure of confidence is determined by using a fourth parameter that is determined on the basis of the degree of influence of the automatic diagnosis made by the diagnosis system on a following therapy for the patient.

In this manner, possible consequences of the automatic diagnosis made by the diagnosis system of the medical image data can be taken into consideration during the determination of the measure of confidence. If it is expected that the automatic diagnosis is likely to entail minor therapeutic consequences, then the measure of confidence can be determined such that more cases are likely to be diagnosed automatically by the diagnosis system. If it is apparent, however, that serious therapeutic consequences for the patient depend on the correct diagnosis of the medical image data, then the measure of confidence can be determined such that the medical image data are presented to a radiologist for a diagnosis or for checking the diagnosis made by the diagnosis system. In this manner the decision already described above can be made using the measure of confidence thus calculated.

In another embodiment, the measure of confidence is determined by using a fifth parameter that is determined on the basis of a current workload in terms of time of radiologists available for performing a diagnosis of the medical image data.

The workload in terms of time of the available radiologist can be acquired electronically and consequently used as an input parameter for calculating the measure of confidence. This procedure is based on the consideration that the measure of confidence can be calculated such that more medical image data are likely to be presented to the radiologist for a diagnosis or for checking the diagnosis if the radiologist has a low workload in terms of time. If the radiologist has a high workload in terms of time, then the measure of confidence can be adjusted such that more cases are presented to the diagnosis system for automatic diagnosis in order to relieve the workload on the radiologist. In this manner the decision described above can be made using the measure of confidence thus calculated.

In another embodiment, the measure of confidence is determined by using a sixth parameter that is determined on the basis of expected costs and/or an anticipated time requirement for the diagnosis of the medical image data by a radiologist.

This procedure is based on the consideration that the decision as to whether the medical image data is diagnosed automatically by the diagnosis system or whether the medical image data is presented to a radiologist for the diagnosis can be made on the basis of a cost calculation, which, for example, compares the costs of manual and automatic diagnosis with one another.

In an embodiment, a proposal for the acquisition of additional medical image data for the patient in support of the automatic diagnosis is automatically generated on the basis of the measure of confidence, wherein the provision of the confidence information involves provision of the proposal.

The acquisition of the additional medical image data is proposed when the measure of confidence indicates that no sufficiently reliable diagnostic assessment can be performed by the automatic diagnosis system on the basis of the existing medical image data. In accordance with the proposal, the additional medical image data can be acquired such that the data exhibit a changed image contrast with respect to the already existing medical image data. The proposal can also be a recommendation to administer a contrast agent to the patient for the acquisition of the additional medical image data.

The provision of the proposal can involve the proposal being displayed to a user on a user interface. The provision of the proposal can also directly involve an additional measurement by means of the medical imaging device in order to acquire the additional medical image data. The proposal can be submitted such that the automatic diagnosis of the additional medical image data, particularly in combination with the existing medical image data, by the diagnosis system exhibits a higher level of reliability of the correct diagnosis than the automatic diagnosis of the existing medical image data alone.

The computer according to the invention has at least one processor configured to execute the method according to the invention.

The computer is thus designed to execute computer readable instructions in order to execute the method according to the invention. The computer has as memory in which computer readable information is stored and the computer is designed to load the computer readable information from the memory and the processor executes the computer readable information in order to execute the method according to the invention.

In this manner the computer according to the invention is designed to execute the method for the provision of confidence information. The computer can have a first provision unit for the provision of the diagnosis system. The computer can furthermore have an acquisition unit for receiving the medical image data for a patient. The computer can also have a determination processor for the determination of a measure of confidence which describes a reliability of a correct diagnosis of the medical image data by the diagnosis system. Finally, the computer can have a second provision unit for the provision of confidence information concerning the reliability of the correct diagnosis of the medical image data by the diagnosis system, wherein the confidence information is based on the determined measure of confidence.

The components of the computer can be designed for the most part in the form of software components. The components, however can also be implemented partly in the form of software-supported hardware components, for example FPGAs or the like, particularly if the calculations in question are very fast. Likewise, the required interfaces can be designed as software interfaces, for example if it is only a question of a transfer of data from other software components. They can also be designed as hardware interfaces, which are driven by suitable software. It is naturally also conceivable for a number of these components to be combined in the form of a single software component or software-supported hardware component.

The medical imaging apparatus according to the invention comprises the computer according to the invention.

The computer can be designed in order to send control signals to the medical imaging apparatus and/or to receive and/or to process control signals in order to execute the method according to the invention. The computer can be integrated into the medical imaging device. The computer can also be installed separately from the medical imaging apparatus. The computer can be connected to the medical imaging apparatus.

The acquisition of the medical image data can be recording the medical image data using a data acquisition scanner of the medical imaging apparatus. The medical image data can then be passed to the computer for further processing. The computer can then receive the medical image data via the acquisition unit.

The present invention also encompasses a non-transitory, computer-readable data storage medium encoded with programming instructions (program code) that, when the storage medium is loaded into a computer or computer system of a medical imaging apparatus cause the computer or computer system to operate the medical imaging apparatus in order to implement any or all of the embodiments of the method according to the invention, as described above.

Examples of electronically readable data media are a DVD, a magnetic tape, a hard drive or a USB stick, on which electronically readable control information, in particular software (cf. above), is stored.

The advantages of the storage medium and the medical imaging apparatus and the computer according to the invention essentially correspond to the advantages of the method according to the invention as explained in detail above. Features, advantages or alternative embodiments mentioned above can likewise also be transferred to the other aspects of the invention. The functional features of the method are embodied by corresponding objective modules, in particular by hardware modules.

DESCRIPTION OF THE PREFERRED EMBODIMENTS

Figures 1, 2:
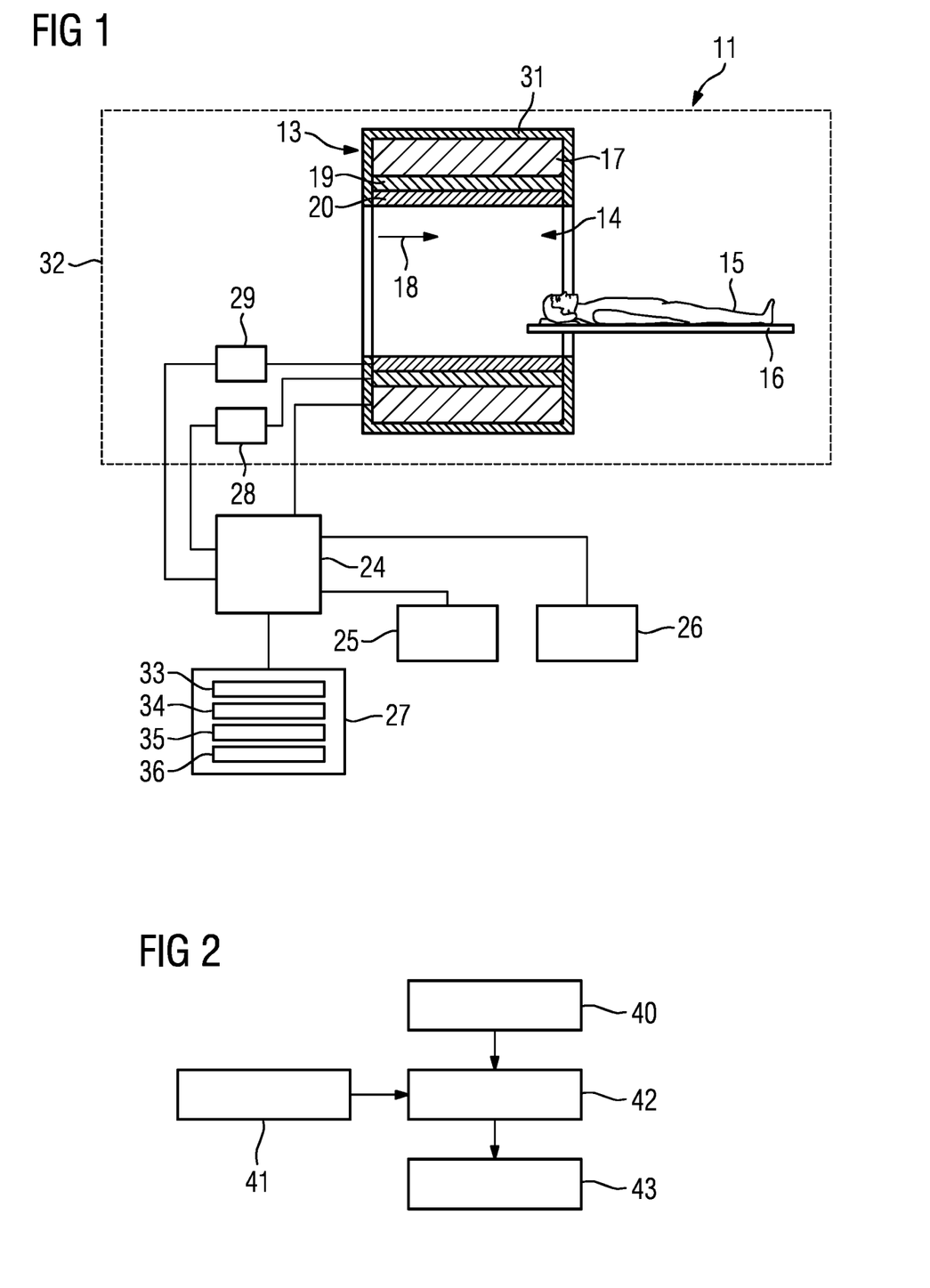
FIG. 1 shows a medical imaging apparatus having a computer according to the invention.
FIG. 2 shows a first embodiment of the method according to the invention.

FIG. 1 shows a medical imaging apparatus having a computer 27 according to the invention.

The medical imaging apparatus can be, for example, a magnetic resonance device, a single-photon emission computed tomography device (SPECT device), a positron emission tomography device (PET device), a computed tomography device, an ultrasound device, an X-ray device or a C-arm device. Combinations of such medical imaging devices are also possible.

In the case shown the medical imaging apparatus is designed as an example as a magnetic resonance apparatus 11.

The magnetic resonance apparatus 11 has a data acquisition scanner 13, having a basic field magnet 17 for generating a strong and constant basic magnetic field 18. The magnetic resonance scanner 13 has a cylindrical patient receiving area 14 for accommodating a patient 15. The patient receiving area 14 is circumferentially enclosed in a cylindrical fashion by the scanner 13. The patient 15 can be moved into the patient receiving area 14 by a patient support 16 that has a patient table that is movable inside the scanner 13. The scanner 13 is shielded externally by a housing shell 31.

The scanner 13 furthermore has a gradient coil arrangement 19 in order to generate magnetic field gradients, which are used for position encoding during an imaging process. The gradient coil arrangement 19 is driven by a gradient controller 28. In addition the scanner 13 has a radio-frequency (RF) antenna 20, which in the case shown is designed as a body coil fixedly integrated into the scanner 13, and a radio-frequency antenna controller 29. The RF antenna 20 is driven by the RF antenna controller 29 so as to radiate radio-frequency magnetic resonance sequences into an examination volume, which is essentially formed by the patient receiving area 14. The radio-frequency sequence excites certain nuclear spins in the patient 15 so as to cause the excited nuclear spins to deviate from the basic magnetic field 18 by an amount known as a flip angle. As those excited nuclear spins relax and return to the steady state, they emit magnetic resonance signals, which are also radio-frequency signals, which are detected by the same antenna from which the excitation sequence was radiated, or by a different antenna.

The magnetic resonance apparatus 11 has a control computer 24 that controls the basic field magnet 17, the gradient controller 28 and the RF antenna controller 29. The control computer 24 provides central control of the magnetic resonance apparatus 11, such as the execution of a predetermined imaging gradient echo sequence. Control information such as imaging parameters, as well as reconstructed magnetic resonance images, can be provided on an output unit 25, in the present case a display monitor, of the magnetic resonance apparatus 11. In addition, the magnetic resonance apparatus 11 has an input unit 26 via which information and/or parameters can be entered by a user during a measurement operation. The control computer 24 can include the gradient controller 28 and/or the RF antenna controller 29 and/or the output unit 25 and/or the input unit 26.

The magnetic resonance apparatus 11 has a recording unit 32 formed by the scanner 13 together with the RF antenna controller 29 and the gradient controller 28.

The illustrated magnetic resonance apparatus 11 can naturally have further components that magnetic resonance apparatuses normally have. The general mode of operation of a magnetic resonance apparatus is known to those skilled in the art, so that a more detailed description is not necessary herein.

The magnetic resonance apparatus 11 as illustrated has a computer 27, which includes a first provision unit 33, an acquisition unit 34, a determination processor 35 and a second provision unit 36. In this manner the computer 27 is configured to execute the method in accordance with FIGS. 2 and 3.

In order for the computer 27 to execute the method alone according to the invention, it will load medical image data via the acquisition unit 34 from a database. If the method according to the invention is executed by a combination of the magnetic resonance apparatus 11 and the computer 27, the acquisition unit 34 of the computer 27 will receive medical image data recorded by the recording unit 32 of the magnetic resonance apparatus 11. To this end the computer 27, in particular the acquisition unit 34, is advantageously connected to the control computer 24 of the magnetic resonance apparatus 11 with regard to data exchange. If the method according to the invention is executed by a combination of the magnetic resonance apparatus 11 and the computer 27, the confidence information determined by the computer 27 can be provided via the provision unit 25 of the magnetic resonance apparatus 11.

FIG. 2 shows a flowchart of a first embodiment of a method according to the invention for the provision of confidence information.

In a first method step 40, a diagnosis system is provided by the first provision unit 33 of the computer 27.

In a further method step 41, medical image data for a patient are received or accessed by the acquisition unit 34 of the computer 27.

In a further method step 42, a measure of confidence, which describes a reliability of a correct diagnosis of the medical image data by the diagnosis system, is determined by the determination processor 35 of the computer 27.

In a further method step 43, confidence information concerning the reliability of the correct diagnosis of the medical image data by the diagnosis system is provided by the second provision unit 36 of the computer 27, wherein the confidence information is based on the determined measure of confidence.

Figure 3:
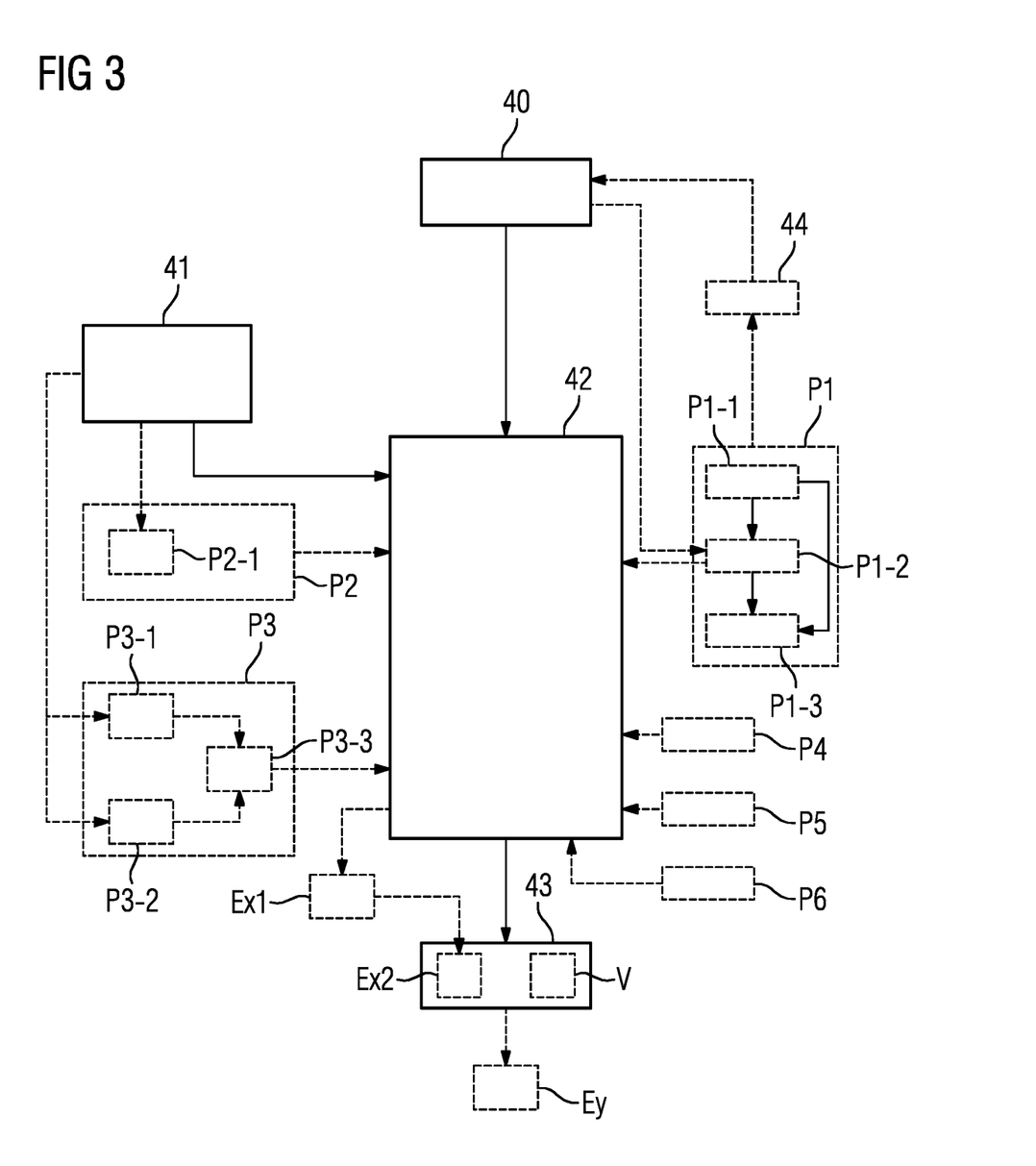
FIG. 3 shows a second embodiment of the method according to the invention.

FIG. 3 shows a flowchart of a second embodiment of a method according to the invention for the provision of confidence information.

The following description is restricted essentially to the differences from the exemplary embodiment in FIG. 2, wherein in respect of method steps remaining the same reference is made to the description of the exemplary embodiment in FIG. 2. Method steps remaining essentially the same are basically identified by the same reference characters.

The embodiment of the method according to the invention shown in FIG. 3 essentially comprises the method steps 40, 41, 42, 43 of the first embodiment of the method according to the invention in accordance with FIG. 2. In addition, the embodiment of the method according to the invention shown in FIG. 3 comprises additional method steps and substeps. Also conceivable is an alternative method sequence to FIG. 3, which involves only a part of the additional method steps and/or substeps illustrated in FIG. 3. An alternative method sequence to FIG. 3 can naturally also involve additional method steps and/or substeps.

In the case shown in FIG. 3 the measure of confidence is determined by using at least one parameter. In this situation one of the aforementioned parameters can be used in determining the measure of confidence. Any desired combination or subset of the aforementioned parameters can also be used simultaneously for determination of the measure of confidence.

The measure of confidence can be determined by using a first parameter, wherein the first parameter characterizes a mean accuracy of the diagnosis system. The first parameter can be determined in a first parameter determination step P1.

The first parameter is determined in the case shown in FIG. 3 by the following substeps P1-1, P1-2, P1-3 of the first parameter determination step P1:

provision of medical training image data in a first substep P1-1, wherein a manual diagnosis by a radiologist exists for the medical training image data, application of the diagnosis system to the medical training image data in a second substep P1-2, wherein an automatic diagnosis of the medical training image data is produced, determination of the first parameter on the basis of a degree of correspondence of the manual diagnosis and automatic diagnosis of the medical training image data in a third substep P1-3.

On the basis of the degree of correspondence of the manual diagnosis and the automatic diagnosis, parameters of the diagnosis system can be adjusted in a further method step 44.

The measure of confidence can also be determined by using a second parameter, wherein the second parameter is determined on the basis of the medical image data for the patient in a second parameter determination step P2. The second parameter determination step P2 can include a substep P2-1 in which a measure of quality for the medical image data is produced on the basis of the medical image data, wherein the second parameter is then determined in the second parameter determination step P2 on the basis of the measure of quality.

The procedure in accordance with FIG. 3 can furthermore provide the determination of a third parameter in a third parameter determination step P3. The measure of confidence can then be defined on the basis of the third parameter.

In this case, a first medical image data set can be diagnosed in a first substep P3-1 and a second medical image data can be diagnosed in a second substep P3-2 set independently of one another by the diagnosis system. In a third substep P3-3, a degree of correspondence of the multiple independent diagnoses can be determined, wherein the third parameter is then determined on the basis of the degree of correspondence of the multiple independent diagnoses.

Generally speaking, the medical image data can include a number of medical image data sets for the patient. The diagnosis system can then separately produce a number of independent diagnoses for the number of medical image data sets, where the measure of confidence is determined by using a third parameter determined in the third parameter determination step P3 on the basis of a degree of correspondence of the multiple independent diagnoses.

In accordance with FIG. 3, the measure of confidence can also be determined by using a fourth parameter, where the fourth parameter is determined in a fourth parameter determination step P4 on the basis of a degree of influence of the automatic diagnosis by the diagnosis system on a following therapy for the patient.

In accordance with FIG. 3, the measure of confidence can also be determined by using a fifth parameter, where the fifth parameter is determined in a fifth parameter determination step P5 on the basis of a current workload in terms of time of radiologists available for performing a diagnosis of the medical image data.

In accordance with FIG. 3, the measure of confidence can also be determined by using a sixth parameter, where the sixth parameter is determined in a sixth parameter determination step P6 on the basis of expected costs and/or an anticipated time requirement for the diagnosis of the medical image data by a radiologist.

Finally, in accordance with FIG. 3, a decision is made in a decision step Ex2, Ey on the basis of the measure of confidence as to whether the medical image data is diagnosed automatically by the diagnosis system or whether the medical image data is presented to a radiologist for the diagnosis. In this case the decision can be made in a first possible decision step Ey, in particular manually, on the basis of the confidence information provided. Alternatively, the decision can be made in a second possible decision step Ex2 automatically on the basis of the measure of confidence. In this case the provision of the confidence information in particular comprises provision of the decision. Furthermore, a threshold value comparison of the measure of confidence with at least one threshold value for the measure of confidence can be performed in a comparison step Ex1 for the second possible decision step Ex2, where the decision is then made in the second possible decision step Ex2 automatically on the basis of the result of the threshold value comparison.

It is furthermore conceivable for a proposal for the acquisition of additional medical image data for the patient in support of the automatic diagnosis to be generated automatically on the basis of the measure of confidence, where the provision of the confidence information in a substep V of the further method step 43 involves provision of the proposal.

The method steps illustrated in FIGS. 2 and 3 of the method according to the invention are executed by the computer 27. To this end the computer 27 has requisite software and/or computer programs, which are stored in a memory of the computer 27. The software and/or computer programs include program code designed in order to execute the method according to the invention when the computer program and/or the software in the computer 27 is executed by the processor of the computer 27.

As an example, execution of parts of the method according to the invention will now be illustrated with a specific case. The following description is naturally intended for illustrative purposes only.

A diagnosis system is assumed that employs an artificial neural deep-learning network as the artificial intelligence. The diagnosis system is designed in order to perform the classification "liver tumor present in patient" in the medical image data.

It can firstly be noted that the "ground truth", in other words the true diagnosis of all diagnosed patients, is in reality not fully known. It is therefore a matter of the diagnosis system being able to replicate the diagnosis of the radiologist as well as possible. In regulatory terms this is referred to as equivalence ("non-inferiority"). Only in a second step would it then be possible to show that the classification by the diagnosis system is better than the existing radiological measures, perhaps through comparison with clinical secondary parameters such as therapy results or pathological or histological information.

In the present example the manual diagnosis by a radiologist is therefore firstly assumed as "ground truth". As a result of the constant comparison of annotated medical training image data and the classification results from the diagnosis system it is for example determined that the diagnosis system replicates the manual diagnostics of the radiology department of the hospital for this particular task with a sensitivity (true positive rate) of 98 percent and a specificity (true negative rate) of 95 percent. Such a determination can take place in the context of the determination of the first parameter described above.

In this particular case it would be appropriate to present the automatic diagnosis made by the diagnosis system to the radiologist at least for confirmation. To exclude the radiologist entirely could be inappropriate in this concrete example because the false negative rate still yields 5 percent incorrect results on average. Such incorrect results can have potentially serious implications for the patient on account of the following therapeutic decision. It is conceivable in this situation that a higher determined measure of confidence means that the radiologist needs to invest less time or attention in the diagnosis or in checking the diagnosis made by the diagnosis system.

In the long term it is conceivable that parts of the diagnostics are also carried out autonomously and automatically by the diagnosis system. In this case the diagnosis can also be trained by the diagnosis system with other "ground truth" methods, such as for example histological and pathological diagnoses. A comparison of the determined confidence by differing automatic diagnosis systems against one another is also possible. It is important that in this scenario the determined measure of confidence for the diagnosis system, in particular on average and in a specific patient case, can be quantitatively documented. From a regulatory viewpoint this can be a decisive step towards the regulatory approval of an automatic diagnosis system.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for providing confidence information, comprising:
   providing a computer with characteristic values of an automatic diagnosis system;
   providing said computer with medical image data acquired from a patient;
   in said computer, determining a measure of confidence that describes a reliability of a correct diagnosis of said medical image data being made by said automatic diagnosis system, wherein the measure of confidence is determined using a parameter that represents a degree of influence of the automatic diagnosis made by the automatic diagnosis system on a subsequent therapy for the patient, and/or represents a current workload, in terms of time, of radiologists available for performing a manual diagnosis of said medical image data, and/or represents an expected value of at least one of a cost and/or a time requirement for manual diagnosis of said medical image data by a radiologist;
   in said computer, generating confidence information, from said determined measure of confidence, that designates the reliability of the correct diagnosis of the medical image data being made by the automatic diagnosis system, and providing said confidence information from said computer as an output in electronic form,
   wherein said medical image data comprise a plurality of medical image data sets each of which is acquired from said patient using an imaging modality, and where said diagnosis system is configured to produce a plurality of independent diagnoses, individually and separately for said plurality of medical image data sets, and comprising, in said computer, determining said measure of confidence using a parameter that represents a degree of correspondence among said plurality of independent diagnoses;
   training the diagnosis system based on medical image training data and corresponding manual diagnosis; and
   in said computer, adjusting at least one parameter of the diagnosis system based on the training, such that said degree of correspondence between the manual diagnosis and the automatic diagnosis made by the automatic diagnosis system is increased.

2. A method as claimed in claim 1 comprising making a decision based on said measure of confidence as to whether the medical image data should be diagnosed automatically by the diagnosis system, or whether the medical image data should be presented to a radiologist for diagnosis.

3. A method as claimed in claim 2 comprising making said decision in said computer based on said confidence information.

4. A method as claimed in claim 2 comprising making said decision automatically n said computer based on said measure of confidence, and providing said decision as an output from said computer in said confidence information.

5. A method as claimed in claim 4 comprising making said decision automatically based on a threshold value comparison of said measure of confidence with at least one reference value for said measure of confidence.

6. A method as claimed in claim 1 comprising determining said first parameter in said computer by:
   receiving medical training image data in said computer, for which a manual diagnosis by the radiologist exists;
   applying the diagnosis system to the medical training image data in order to obtain an automatic diagnosis of the medical training image data; and
   determining said parameter based on a degree of correspondence of the manual diagnosis and the automatic diagnosis of the medical training image data.

7. A method as claimed in claim 1 comprising determining said measure of confidence in said computer using a parameter determined from said medical image data.

8. A method as claimed in claim 7 comprising, in said computer, determining a measure of quality for the medical image data based on the medical image data, and using said measure of quality as said parameter based on said medical image data.

9. A method as claimed in claim 1 comprising generating, in said confidence information, a proposal for acquisition of additional medical image data for the patient to support an automatic diagnosis by the diagnosis system.

10. A method as claimed in claim 1 wherein each of said medical image data sets is recorded from the same patient.

11. A method as claimed in claim 1 wherein said plurality of medical image data sets are recorded sequentially in one recording session.

12. A method as claimed in claim 1 wherein said plurality of medical image data sets are recorded using differing imaging modalities.

13. A method as claimed in claim 1 wherein said plurality of medical image data sets are recorded simultaneously in a case of integrated imaging devices.

14. A computer for providing confidence information, comprising:
   a processor provided with characteristic values of an automatic diagnosis system;
   said processor also being provided with medical image data acquired from a patient;
   said processor being configured to determine a measure of confidence that describes a reliability of a correct diagnosis of said medical image data being made by said automatic diagnosis system, wherein the measure of confidence is determined using a parameter that represents a degree of influence of the automatic diagnosis made by the diagnosis system on a subsequent therapy for the patient, and/or represents a current workload, in terms of time, of radiologists available for performing a manual diagnosis of said medical image data, and/or represents an expected value of at least one of a cost and/or a time requirement for manual diagnosis of said medical image data by a radiologist;
   said processor being configured to generate confidence information, from said determined measure of confidence, that designates the reliability of the correct diagnosis of the medical image data being made by the automatic diagnosis system, and to provide said confidence information from said computer as an output in electronic form, wherein said medical image data comprise a plurality of medical image data sets each of which is acquired from said patient using an imaging modality, and said plurality of medical image data sets exhibiting differing image contrasts, and where said diagnosis system is configured to produce a plurality of independent diagnoses, individually and separately for said plurality of medical image data sets, and comprising, in said computer, determining said measure of confidence using a parameter that represents a degree of correspondence among said plurality of independent diagnoses;

said processor being configured to train the diagnosis system based on medical image training data and corresponding manual diagnosis; and said processor being configured to adjust at least one parameter of the diagnosis system based on the training, such that said degree of correspondence between the manual diagnosis and the automatic diagnosis made by the automatic diagnosis system is increased.

15. A computer as claimed in claim 14 wherein said computer is configured to determine said measure of confidence using a parameter determined from said medical image data.

16. A medical imaging apparatus comprising:
a medical image data acquisition scanner;
a computer provided with characteristic values of an automatic diagnosis system;
said computer being provided with medical image data acquired from a patient by said scanner;
said computer being configured to determine a measure of confidence that describes a reliability of a correct diagnosis of said medical image data being made by said automatic diagnosis system, wherein the measure of confidence is determined using a parameter that represents a degree of influence of the automatic diagnosis made by the diagnosis system on a subsequent therapy for the patient, and/or represents a current workload, in terms of time, of radiologists available for performing a manual diagnosis of said medical image data, and/or represents an expected value of at least one of a cost and/or a time requirement for manual diagnosis of said medical image data by a radiologist;
said computer being configured to generate confidence information, from said determined measure of confidence, that designates the reliability of the correct diagnosis of the medical image data being made by the automatic diagnosis system, and to provide said confidence information from said computer as an output in electronic form,
wherein said medical image data comprise a plurality of medical image data sets each of which is acquired from said patient using an imaging modality, and each of said plurality of medical image data sets recorded using the same imaging modality, and where said diagnosis system is configured to produce a plurality of independent diagnoses, individually and separately for said plurality of medical image data sets, and comprising, in said computer, determining said measure of confidence using a parameter that represents a degree of correspondence among said plurality of independent diagnoses;

said computer being configured to train the diagnosis system based on medical image training data and corresponding manual diagnosis; and said computer being configured to adjust at least one parameter of the diagnosis system based on the training, such that said degree of correspondence between the manual diagnosis and the automatic diagnosis made by the automatic diagnosis system is increased.

17. A medical imaging apparatus of claim 16 wherein said computer is configured to determine said measure of confidence using a parameter determined from said medical image data.

18. A non-transitory, computer-readable data storage medium encoded with programming instructions, said storage medium being loaded into a computer and said programming instructions causing said computer to:
receive characteristic values of an automatic diagnosis system;
receive medical image data acquired from a patient;
determine a measure of confidence that describes a reliability of a correct diagnosis of said medical image data being made by said automatic diagnosis system, wherein the measure of confidence is determined using a parameter that represents a degree of influence of the automatic diagnosis made by the diagnosis system on a subsequent therapy for the patient, and/or represents a current workload, in terms of time, of radiologists available for performing a manual diagnosis of said medical image data, and/or represents an expected value of at least one of a cost and/or a time requirement for manual diagnosis of said medical image data by a radiologist;
generate confidence information, from said determined measure of confidence, that designates the reliability of the correct diagnosis of the medical image data being made by the automatic diagnosis system, and provide said confidence information from said computer as an output in electronic form,
wherein said medical image data comprise a plurality of medical image data sets each of which is acquired from said patient using an imaging modality, and said plurality of medical image data sets is recorded by magnetic resonance imaging by differing magnetic resonance sequences, and where said diagnosis system is configured to produce a plurality of independent diagnoses, individually and separately for said plurality of medical image data sets, and comprising, in said computer, determining said measure of confidence using a parameter that represents a degree of correspondence among said plurality of independent diagnoses;
train the diagnosis system based on medical image training data and corresponding manual diagnosis; and
adjust at least one parameter of the diagnosis system based on the training, such that said degree of correspondence between the manual diagnosis and the automatic diagnosis made by the automatic diagnosis system is increased.

* * * * *